United States Patent
Hirt et al.

(10) Patent No.: US 10,233,150 B2
(45) Date of Patent: Mar. 19, 2019

(54) COMPOSITION FOR THE MODULATION OF THE ACTIVITY OF NON-STRUCTURE PROTEINS

(71) Applicant: Eberhard Karls Universitaet Tuebingen Medizinische Fakultaet, Tuebingen (DE)

(72) Inventors: Bernhard Hirt, Tuebingen (DE); Claus Zeyher, Tuebingen (DE); Corinna Gleiser, Rottenburg (DE); Lothar Just, Tuebingen (DE)

(73) Assignee: Eberhard Karls Universitaet Tuebingen Medizinische Fakultaet, Tuebingen (DE)

( * ) Notice: Subject to any disclaimer, the term of this patent is extended or adjusted under 35 U.S.C. 154(b) by 0 days.

(21) Appl. No.: 15/418,903

(22) Filed: Jan. 30, 2017

(65) Prior Publication Data
US 2017/0137379 A1     May 18, 2017

Related U.S. Application Data

(63) Continuation of application No. PCT/EP2015/067113, filed on Jul. 27, 2015.

(30) Foreign Application Priority Data

Jul. 30, 2014  (DE) .................. 10 2014 110 783

(51) Int. Cl.
| | | |
|---|---|---|
| *A01N 1/02* | (2006.01) | |
| *C07D 207/28* | (2006.01) | |
| *A01N 43/36* | (2006.01) | |
| *A01N 43/48* | (2006.01) | |
| *A61K 8/49* | (2006.01) | |
| *A61Q 19/00* | (2006.01) | |
| *C07D 403/06* | (2006.01) | |
| *C07D 487/10* | (2006.01) | |

(52) U.S. Cl.
CPC ......... *C07D 207/28* (2013.01); *A01N 1/0226* (2013.01); *A01N 43/36* (2013.01); *A01N 43/48* (2013.01); *A61K 8/494* (2013.01); *A61K 8/4913* (2013.01); *A61Q 19/00* (2013.01); *C07D 403/06* (2013.01); *C07D 487/10* (2013.01)

(58) Field of Classification Search
None
See application file for complete search history.

(56) References Cited

U.S. PATENT DOCUMENTS

| | | | | |
|---|---|---|---|---|
| 3,948,943 A | * | 4/1976 | Eberhardt | ................ A61K 8/44 548/537 |
| 4,053,588 A | * | 10/1977 | Konig | ................ C07K 5/06173 514/17.5 |
| 4,652,585 A | | 3/1987 | Gerhardt et al. | |
| 7,994,251 B2 | | 8/2011 | Rogmann et al. | |
| 2006/0257498 A1 | * | 11/2006 | Stingl | .................... A01N 33/04 424/616 |

FOREIGN PATENT DOCUMENTS

| | | |
|---|---|---|
| DE | 3410956 A1 | 9/1985 |
| DE | 19603977 A1 | 8/1997 |
| DE | 20017213 U1 | 12/2000 |
| EP | 156275 A2 | 10/1985 |
| JP | 51-035433 | 3/1976 |
| JP | 09-315946 | 12/1997 |
| JP | 2009-215267 A | 9/2009 |
| WO | WO-02/50205 | 6/2002 |
| WO | WO-2012/028196 A1 | 3/2012 |

OTHER PUBLICATIONS

Database Registry Chemical Abstracts Service, Columbus, Ohio, Accession No. RN 126646-23-9, 126646-24-0, Entered STN: Apr. 20, 1990.*
Search Report and Written Opinion in International Application No. PCT/EP2015/067113 dated Sep. 28, 2015, 6 pages.
Von Rheinbaben et al., "Glucoprotamin ED", Wallhäußers Praxis der Sterilisation, Desinfektion, Antiseptik und Konservierung, 6 Edition, 1999, Stuttgart, Georg Thieme, pp. 786-787.
Meyer et al., Efficacy of Glucoprotamin® Containing Disinfectants Against Different Species of Atypical Mycobacteria; Journal of Hospital Infection, 42(2), 1999, pp. 151-154.
Kapprell et al., Development of a Fluorescence Resonance Energy Transfer Peptide Library Technology for Detection of Protease Contaminants in Protein-Based Raw Materials Used in Diagnostic Assays; Assay and Drug Development Technologies, vol. 9, No. 5, Oct. 2011, pp. 549-553.
Steger et al., "Hepatitis-C-Virus, Römpp Lexikon Chemie, Stichwork: Hepatitis-C-Virus, Zeitrang", Letzte Aktualisierung, Apr. 2012, http://roempp.thieme.de, retrieved from the internet on May 6, 2015, 3 pages.
Non Structure Protein, http://archiv.c6-magazin.de/06/news/?neuigkeit=6997, retrieved from the internet on May 6, 2016.
Examination Report in German Application No. 10 2014 110 783.7 dated Jun. 17, 2015, 25 pages.

* cited by examiner

*Primary Examiner* — Samantha L Shterengarts
(74) *Attorney, Agent, or Firm* — Marshall, Gerstein & Borun LLP

(57) ABSTRACT

The present invention relates to a composition for the modulation of the activity of non-structure proteins and a compound contained therein.

6 Claims, 7 Drawing Sheets

COMPOSITION FOR THE MODULATION OF THE ACTIVITY OF NON-STRUCTURE PROTEINS

CROSS-REFERENCES TO RELATED APPLICATIONS

This application is a continuation of co-pending international patent application PCT/EP2015/067113 field on 27 Jul. 2015 and designating the U.S., which has been published in German, and claims priority from German patent application DE 10 2014 110 783.7 filed on 30 Jul. 2014. The entire contents of these prior applications are incorporated herein by reference.

FIELD

The present invention relates to a composition for the modulation of the activity of non-structure proteins and to a compound contained therein.

BACKGROUND

The modulation, in particular the inhibition of the activity of proteins is of central significance in various fields of science, medicine, and technology.

In the cell and tissue preservation it is important for a permanent storage of respective preparations to completely inactivate the activity of such proteins which exert functional or catalytic functions in order to prevent the tissue degradation. At the same time, structure proteins need to remain intact to preserve the integrity and the shape of the biological material. Also in the field of the preservation of pharmaceutical preparations or food or animal feed products, the inhibition of functional or non-structure proteins is significant for a lasting durability.

The inactivation of functional proteins also plays a central role in the field of technical fermentation and bioprocess engineering, the life and agricultural sciences and in medical applications, for example in connection with the inactivation of toxines, hormones, and inflammation mediators.

In the state of the art for the modulation or inhibition of the activity of non-structure proteins, in particular of enzymes, use is made of aldehyde such as the formaldehyde, or detergents with demonstrated denaturating effect on proteins such as the sodium dodecyl sulfate (SDS), or other ionic tensides with a chain length of $C_{12}$. However, aldehydes have a high acute toxicity. They are deemed to be carcinogenic, mutagenic, and strongly sensitizing. For this reasons, in recent times aldehydes have again been the subject of criticism. Furthermore, aldehydes do not only have a strong effect on proteins with enzymatic activity but also on structure proteins by changing their structure via crosslinking. SDS and ionic surfactants with a chain length of C12 tend to precipitate and therefore to lose their activity in an environment of an increased electrolyte concentration, in particular in connection with metal ions such as $Ca^{++}$, $Mg^{++}$ or $K^+$. For this reason, they are inappropriate for a use in complex biological systems. The strongly denaturating acting detergents are also said to be highly sensitizing and therefore hazardous to health. Detergents which are not strongly denaturating, such as fatty alcohols like Triton X100, are not appropriate for the inactivation of functional proteins and just for this reason they are used for protein solubilization.

SUMMARY

Against this background, it is an object of the present invention to provide a new composition or a new active agent, which are appropriate for the modulation of the activity of non-structure proteins, however, do not comprise the disadvantages of the compositions or compounds which are currently used in the state of the art.

DETAILED DESCRIPTION

This object is met by a composition which comprises a 5-oxo-pyrrolidine-2-carboxylic acid derivative with the formula I

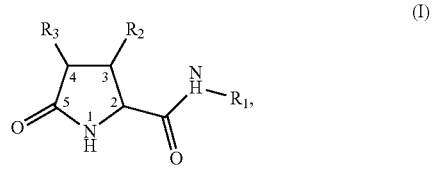

where
$R_1$ is selected from the group consisting of:
linear alkyl residue with $C_1$-$C_6$,

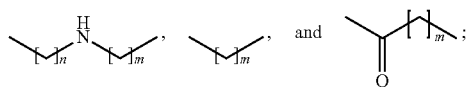

$R_2$ and $R_3$ are selected from the group consisting of:

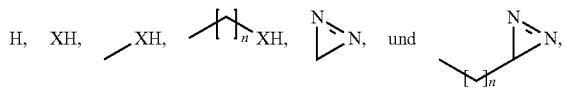

each with:
n=0-20,
m=1-25, and
X=O or S;
for the modulation of the activity of non-structure proteins.

This object is also met by a 5-oxo-pyrrolidine-2-carboxylic acid derivative with the formula (I) which is set out above.

As the inventors were able to realize a 5-oxo-pyrrolidine-2-carboxylic acid derivative has excellent characteristics to modulate the activity of non-structure proteins. At the same time, the 5-oxo-pyrrolidine-2-carboxylic acid derivative is only of health concern which is significantly less than for the currently used aldehydes or deter-gents or surfactants.

It has proved to be an advantage that the identified effects are dose-dependent. For this reason, the modulation of the activity of the non-structure proteins can be adjusted to the intended strength and duration in a targeted manner and opens up a large number of application possibilities.

5-oxo-pyrrolidine-2-carboxylic acid derivatives can be produced according to methods which are generally known in the state of the art, for example according to a method described in the DE 3 410 956. Furthermore, the inventors were able to develop a new method for the production of 5-oxo-pyrrolidine-2-carboxylic acid derivatives which is associated with even less production expenses.

According to the invention, a "derivative" of 5-oxo-pyrrolidine-2-carboxylic acid is a descendant thereof which can be obtained therefrom by chemical modification. The derivatives still comprise the heterocycle of pyrrolidine, however, may differ from each other in particular with respect to their alkyl residues. In the derivatives the heterocycle of the pyrrolidine can comprise functional groups at various positions, such as preferably at the positions 3 and 4. According to the invention, both the S enantiomer and the R enantiomer or the racemate formed thereof are encompassed. The "5-oxo-pyrrolidine-2-carboxylic acid derivative" does also encompass a 5-oxo-pyrrolidine-2-carbon ester derivative which is also referred to as pyroglutamate ester derivative.

According to the invention, "non-structure proteins" refer to such proteins which do not function as structural materials in tissues or cells of living beings. Non-structure proteins are for this reason in particular such proteins with catalytic functions, such as enzymes, but also peptides, peptide hormones, receptors, cytokines, peptidic toxines etc.

According to the findings of the inventors, the invention is also appropriate for the modulation of the catalytic activity of nucleic acid molecules, such as ribozymes, aptamers, siRNA etc., and the activity of steroid hormones.

According to the invention, a "modulation" relates to a change. A "modulation of the activity of non-structure proteins" is therefore to be understood as a targeted change of the function of the proteins in their natural environment.

The features, characteristics, advantages and further developments of the composition according to the invention do also apply to the 5-oxo-pyrrolidine-2-carboxylic acid derivative in correspondence.

The object underlying the invention is herewith completely met.

According to a particular embodiment of the composition according to the invention or the 5-oxo-pyrrolidine-2-carboxylic acid derivative according to the invention, the modulation is an inhibition, preferably a deactivation.

This measure has the advantage that protein activities, for example of enzymatic or catalytic kind, can be reduced or even switched off in a targeted manner, while structure proteins are still in the position to give cells their shape and tissues their stability and elasticity. This is especially important in the field of cell and tissue preservation.

In another embodiment of the invention the non-structure protein is an enzyme.

Also this measure has the advantage that the composition according to the invention or the 5-oxo-pyrrolidine-2-carboxylic acid derivative according to the invention inhibits or switches off catalytic activities in a targeted manner, whereas structure proteins still exert their biomechanical and physical properties.

It is preferred according to the invention if the enzyme is selected from the group consisting of: oxidoreductase, such as alcohol dehydrogenases; hydrolases, such as alkalic phosphatase, endoproteases, RNases, DNases, lipases; transferases; lyases; isomerases; ligases.

This measure has the advantage that such enzymes are inhibited or completely switched off in a targeted manner, which are of significant importance in the field of the preservation or medical implications.

In another embodiment of the invention the 5-oxo-pyrrolidine-2-carboxylic acid derivative is glucoprotamin with the formula II:

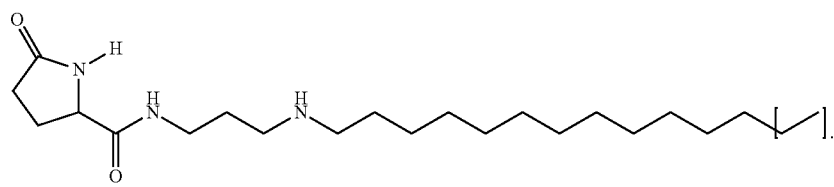

(II)

By this measure, such a 5-oxo-pyrrolidine-2-carboxylic acid derivative is employed which in the state of the art is so far used as a surface disinfectant, primarily in the clinic. Glucoprotamin is a substance consisting of several components. The most important two components and main active agents of glucoprotamin are the (2S)-pyrrolidine-5-oxo-carboxylic acid amide, N-3-(dodecylamino)-propyl and the (2S)-pyrrolidine-5-oxo-carboxyclic acid amide, N-3-(tetradecylamino)propyl. Glucoprotamin (CAS-No. 164907-72-6) is also referred to as amine, N-C12-14-alkylpropylenedi-, L-glutamate. In the formula (II) the parenthesis symbolizes that there can be long or short chain alkyl residues, in particular C12 and C14, which exist in a mixture. With a C12 residue glucoprotamin has the molecular formula $C_{20}H_{39}N_3O_2$ and the molecular weight of 353.55, with a C14 residue it has the molecular formula $C_{22}H_{43}N_3O_2$ and the molecular weight of 381.61.

Glucoprotamin is characterized by its insensitivity against a high load of protein, a low toxicity or ecotoxicity, respectively, it can be rapidly and completely degraded. It is readily soluble in water and stable over a long time. In a study no losses of activity could be demonstrated even after eight years of storage. It is marketed for example by the company Ecolab Germany GmbH, Düsseldorf.

The suitability of glucoprotamin according to the invention was surprising and not to be expected. In the state of the art the mechanism of the disinfecting activity is postulated as being the destruction of the membrane of the cytoplasm of bacterial cells and of the envelope of enveloped viruses; Meyer and Kluin (1999), Efficiency of glucoprotamin-containing disinfectants against different species of atypical microbacteria, J. Hosp. Infect. 42(2), pages 151-154. The activity on naked lipophilic viruses is explained with an interaction with lipophilic groups in the protein capsid of the particles; cf. von Rheinbaben and Meyer (2008), Glucoprotamin. In: Kramer and Assadin (Eds.), Wallhäußers Praxis der Sterilisation, Desinfektion, Antiseptik and Konservierung, 6. Edition, Stuttgart, New York: Georg Thieme Verlag KG, pages 786-787.

The suitability of glucoprotamin for the modulation and inhibition of the activity of non-structure proteins is neither described nor rendered obvious in the state of the art.

In another embodiment of the invention the composition according to the invention or the 5-oxo-pyrrolidine-2-carboxylic acid derivative is provided for a use as a preservation and/or fixation agent.

The inventors could demonstrate that the composition and the 5-oxo-pyrrolidine-2-carboxylic acid derivative is appropriate for the preservation of tissues, organs and full body preparations without using aldehyde. The comprehensive and simultaneous inactivation of several classes of enzymes which play a role in the lysis of tissues allows a new kind of preservation of biological material. The inventors could demonstrate in their experiments that both organ and full body preparations are barely changed in their structural integrity after a treatment with the composition according to the invention. Even after several months the full body preparations could be preserved with realistic haptics in a quality which has never been reached so far.

The characteristic which was found by the inventors make the composition and the 5-oxo-pyrrolidine-2-carboxylic acid derivative predestined also for a preservation agent for cosmetics, food or pharmaceutical products.

According to an embodiment of the invention the composition and the 5-oxo-pyrrolidine-2-carboxylic acid derivative are configured for a use as a pharmaceutical composition.

The inhibiting activity on non-structure proteins which was found by the inventors makes the composition and the 5-oxo-pyrrolidine-2-carboxylic acid derivative especially suitable for a use as a pharmaceutical preparation. The composition according to the invention and the 5-oxo-pyrrolidine-2-carboxylic acid derivative can be used for the inhibition of the activity of hormones, antibodies, cytokines, interferons, interleukins, chemokines, growth factors, colony stimulating factors, tumor necrosis factors, receptors, ribozymes, and other disease-mediating enzymes in a targeted manner.

The invention can be used against chronic inflammatory diseases in a targeted manner, e.g. by creating a deinflammatory environment, for example against chronic rheumatoid arthritis. This can for example be effected by an intraarticular injection of the composition or the 5-oxo-pyrrolidine-2-carboxylic acid derivative according to the invention or a lavage herewith. Other examples are chronic inflammatory bowel diseases, such as Morbus Crohn or Collitus ulcerosa, chronic obstructive lung disease, chronic skin and mucosa diseases, or autoimmune diseases.

Also in an acute inflammatory process the invention is deployed, for ex-ample in the context of a wound debridement or a lavage.

The composition and the 5-oxo-pyrrolidine-2-carboxylic acid derivative can also be used in the field of oncology, immunology, and allergology, for example for the inactivation of cytokines or chemokines or for the inactivation of hormones.

Also in the field of cosmetics and personal care or the anti-aging, the composition and the 5-oxo-pyrrolidine-2-carboxylic acid derivative according to the invention are applied. They can be used for inactivating odor-producing enzymes and thus can be used as a component of deodorants. In addition, by means of the composition or the 5-oxo-pyrrolidine-2-carboxylic acid derivative according to the invention elastases and/or collagenases can be inactivated in a targeted manner and by doing so signs of aging of the skin can be prevented. The composition and the 5-oxo-pyrrolidine-2-carboxylic acid derivative according to the invention can therefore be used as a component of creams, ointments, lotions and other topically applicable formulations.

According to a preferred embodiment of the invention the composition or the 5-oxo-pyrrolidine-2-carboxylic acid derivative are configured for a use as a biocide, preferably selected from the group consisting of: insecticide, ovicide, acaricide, molluscicide, nematicide, anthelmintic, herbicide, algicide, graminicide, and arboricide.

This measure has the advantage that the composition and the 5-oxo-pyrrolidine-2-carboxylic acid derivative can be used in a targeted application in the life and agricultural sciences and can there show effects because of their modulating or inhibiting activity on non-structure proteins, especially on enzymes, in a targeted manner. The organism is shut down in its metabolic activity by a targeted inhibition of its non-structure proteins and as a consequence loses its damaging effects.

According to a preferred embodiment the composition according to the invention and the 5-oxo-pyrrolidine-2-carboxylic acid derivative according to the invention are configured for a use as a fermentation auxiliary agent.

By this measure, a targeted application of the invention in the food and semiluxury food production is realized. By the targeted inhibition of the fermentation enzymes the fermentation process can be precisely controlled. Also the use in technical fermentation and bioprocess engineering, in particular in the bioethanol, chemicals or pharmaceutical production, the silage technology, in biogas plants or bioreactor plants, are encompassed by the invention.

Also in the field of tissue engineering the composition and the 5-oxo-pyrrolidine-2-carboxylic acid derivative according to the invention are used by creating an enzyme-free and anti-inflammatory environment.

According to a preferred embodiment of the invention, the composition and the 5-oxo-pyrrolidine-2-carboxylic acid derivative is configured as a surface coating agent.

Functional groups, such as OH, SH or photoreactive groups, can be attached for example at the positions 3 and 4 of the pyrrolidine ring. This allows the use of the 5-oxo-pyrrolidine-2-carboxylic acid derivative and a composition according to the invention as a surface coating in the product development and application in the fields of medicine and biotechnology. In this context it is especially thought of coated medical devices such as thread materials, stents, joint implants, and wound dressings. The coating can be realized for example via adhesion but also via covalent binding or immobilization of the 5-oxo-pyrrolidine-2-carboxylic acid derivative.

It goes without saying that the features mentioned before and those to be explained in the following cannot only be used in the combination indicated in each case but also in other combinations or in isolated position without departing from the scope of the invention.

The present invention is now explained by means of embodiments in more detail which will result in further features, characteristics, and advantages. The embodiments are purely illustrative and do not restrict the scope of the invention.

EXAMPLES

Figure 1:
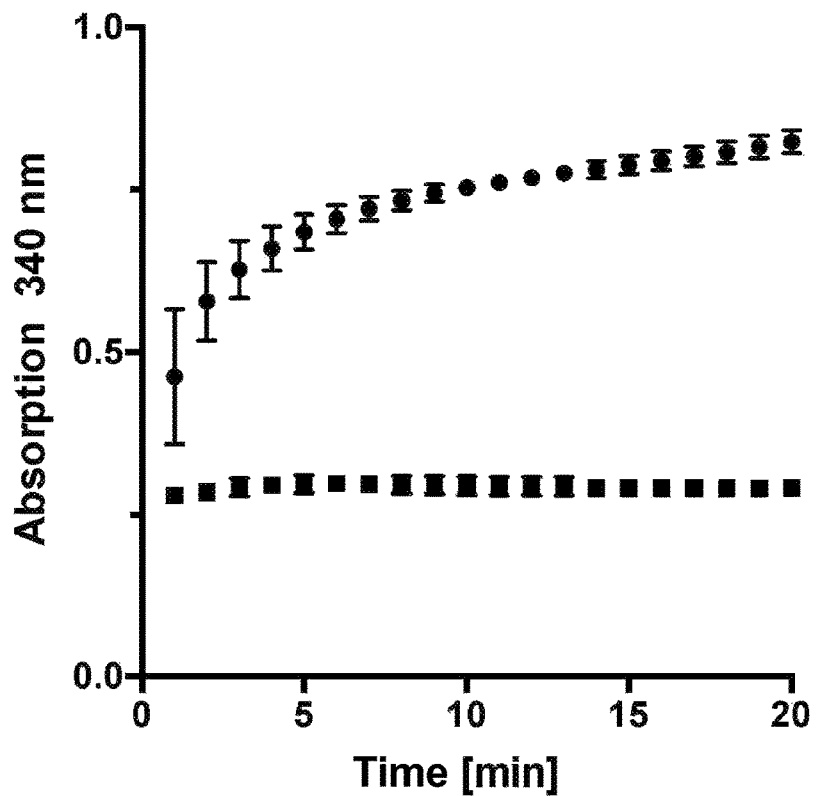
FIG. 1: Reaction process of the reaction of alcohol dehydrogenase (ADH). The ADH is completely inhibited by glucoprotamin (squares; n=3; error bars=SEM). The kinetics of the control without glucoprotamin (circles; n=3; error bar=SEM) show that the substrate/coenzyme which were used in the test were present in saturating concentration.

1. Production of the 5-oxo-pyrrolidine-2-carboxylic acid Derivative

The production of the 5-oxo-pyrrolidine-2-carboxylic acid derivative is described in the DE 34 10 956 by the way of the example of glucoprotamin, the content of this document is incorporated herein and made to the subject of the present application.

In addition, the inventors have developed an improved method for the production of a 5-oxo-pyrrolidine-2-carboxylic acid derivative.

The reaction takes place with the starting substances

I. 5-oxo-pyrrolidine-2-carboxylic acid derivatives (preferably the S enantiomer, but also the R enantiomer or racemate) and II. N substituted monoamines (2.3) and/or diamines (2.2) and/or fatty amides (2.3).

a) Conversion of 5-oxo-pyrrolidine-2-carboxylic acid derivatives with N substituted monoamines

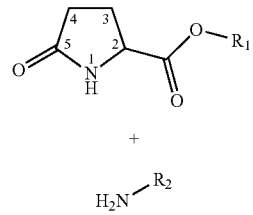

Definition of the residues:
$R_1$=linear alkyl residue with $C_{1-6}$; preferably $C_1$;
$R_2$=linear alkyl residue with the chain length $C_{2-22}$, wherein mono and polyunsaturated alkyl residues are included.

Scheme 1: Conversion of the 5-oxo-pyrrolidine-2-carboxylic acid derivatives with N substituted monoamines The reaction only requires a preferred temperature of 60° C., a preferred reaction time of 60 min and a preferred pressure of 300-350 mbar. Methanol is distilled off.

b) Conversion of the 5-oxo-pyrrolidine-2-carboxylic acid Derivatives with N Substituted Diamines

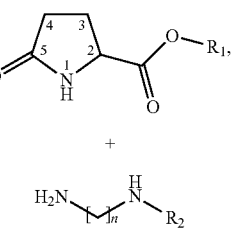

Definition of the residues:

n=1-6, $R_1$=linear alkyl residue with $C_{1-6}$; preferably $C_1$;

$R_2$=linear alkyl or acyl residue with the chain length $C_{2-22}$, wherein mono and polyunsatured alkyl and acyl residues are included.

Scheme 2: Conversion of the 5-oxo-pyrrolidine-2-carboxylic acid Derivatives with N Substituted Diamines Scheme 4: Synthesis of glucoprotamin from 5-oxo-pyrrolidine-2(S)-caboxylic acid methylester and cocospropylene-1,3-diamine

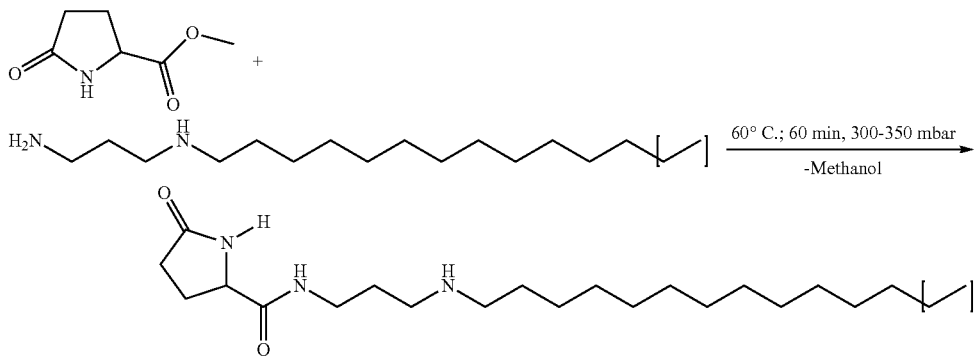

The reaction only requires a preferred temperature of 60° C., a preferred reaction time of 60 min and a preferred pressure of 300-350 mbar. Methanol is distilled off.

c) Conversion of the 5-oxo-pyrrolidine-2-carboxylic acid Derivatives with N Substituted Fatty Amides

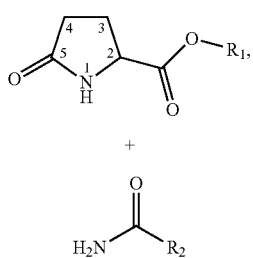

Definition of the residues:

$R_1$=linear alkyl residue with $C_{1-6}$; preferably $C_1$ $R_2$=linear alkyl residue with the chain length $C_{2-24}$, wherein mono and polyunsatured alkyl residues are included.

Scheme 3: Conversion of the 5-oxo-pyrrolidine-2-carboxylic acid Derivatives with N Substituted Fatty Amides The reaction only requires a preferred temperature of 60° C., a preferred reaction time of 60 min and a preferred pressure of 300-350 mbar. Methanol is distilled off.

With this new method the inventors succeeded in producing the 5-oxo-pyrrolidine-2-carboxylic acid derivative referred to as glucoprotamin.

The two active substances subsumed under the active agent glucoprotamin, i.e. (2S)-pyrrolidine-5-oxo-carboxylic acid amid, N-3-(dodecylamino)propyl and (2S)-pyrrolidine-5-oxo-carboxylic acid amid, N-3-(tetradecylamino)propyl, in the method according to the invention are not generated by the reaction of the linear starting substance L-glutamic acid or its ester derivatives and the fatty amine mixture do-decyl/tetradecylpropylidene diamine, also referred to as cocospropylene-1,3-diamine, but by the reaction of the already cyclic starting product 5-oxo-pyrrolidine-2(S)-carboxylic acid methylester, also referred to as L-pyroglutamate methylester, with cocospropylene-1,3-diamine only at approximately 60° C., approximately 60 min and approximately 300 to 350 mbar and by distilling off of methanol.

For this purpose, 251 g (1 mol) cocospropylene-1,3-diamine (CAS-No. 6171-63-7) (70 mol % dodecylpropylene diamine, 30 mol % tetradecylpropylene diamine) were melted in the water bath at 60° C. Then 143.14 g (1 mol) 5-oxo-pyrrolidine-2(S)-carboxylic acid methylester were added and brought to reaction at a reduced pressure of 330 mbar in a rotary evaporator for 1 hour at 60° C. The methanol generated in the reaction (32 g) was distilled off. The conversion product was liquid-viscose at 60° C. and solidified at room temperature to a beige-yellow waxy paste. The melting temperature of the conversion product is 60-70° C.

The analysis of the synthesized product confirms the substance of glucoprotamin. The results of the high resolution mass spectrometry showed a mass deviation of the test substance of only 0.01 to 0.04 ppm of the theoretical masses of [M+H]+=253 g/mol (2S)-pyrrolidine-5-oxo-carboxylic acid amid, N-3-(dodecylamino)propyl and [M+H]+=286 g/mol (2S)-pyrrolidine-5-oxo-carboxylic acid amid, N-3-(tetradecylamino)propyl.

A 1H and 13C NMR structure analysis showed the correspondence with the theo-retically predicted spectra (Scifinder/ChemDraw 13.0).

The new production method allows due to its mild reaction conditions the use of long chain and/or unsaturated and thus vulnerable carbon chains without running the risk of a disintegration or oxidation in the context of the synthesis reaction. Furthermore, in the new production method "chemically assembled" starting substances can be used. Also complex chemical reactions become possible without influencing the synthesis reaction.

d) Modification of the 5-oxo-pyrrolidine-2-carboxylic derivatives

The starting substances 5-oxo-pyrrolidine-2-carboxylic acid derivatives and N substituted monoamine, diamine and fatty amid derivatives should be modified with the objection to take influence on the kinetics of the active agent, the dynamics of the active agent, and the performance of the active agent of the synthesis products.

The starting substance 5-oxo-pyrrolidine-2-carboxylic acid can be modified at the positions 3 and 4 of the pyrrolidine ring.

The attachment of for example protected hydroxyl or sulfhydryl groups at the positions 3 and/or 4 of the pyrrolidine ring allows the coupling of the active substance to surfaces of various materials. This allows the use of the produced active agents as a surface coating.

Scheme 5: Modification of the 5-oxo-pyrrolidine-2-carboxylic acid derivative by attaching (a) hydroxyl and/or (b) sulfhydryl groups. It is shown the example of a hydroxyl group at position 4 and sulfhydryl group at the position 3. $R_1$ stands for a linear alkyl residue with $C_{1-6}$; prefrably $C_1$.

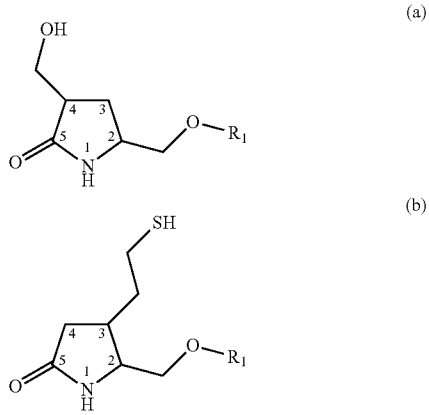

The attachment of for example photoreactive groups can allow a conditioned modification of the active substance Scheme 6: Modification of the 5-oxo-pyrrolidine-2-carboxylic acid derivative by the attachment of photoactive groups. Shown are two examples at the position 3 and position 4. $R_1$ stands for a linear alkyl residue with $C_{1-6}$; prefrably $C_1$.

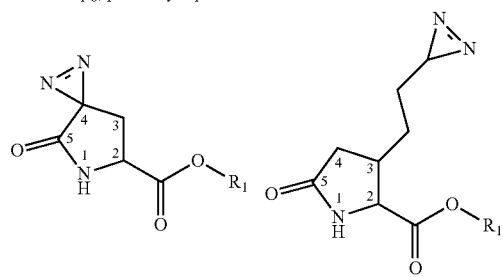

The mild new production method also allows for example the use of alkyl residues with various chain lengths and also in unsaturated state. A modification of the chain length can result in a changed profile of the active agent.

(1) Diamines, (2) monoamines, (3) fatty amides

with $R_2=$
 linear alkyl residue with the chain length of $C_{2-22}$
 mono and/or polyunsaturated alkyl residues
 in (1) also mono- and/or polyunsaturated acyl residues
 n=1-6

Scheme 7: Presentation of Modified Monoamine, Diamine and Fatty Amid Groups.

2. Modulation/Inactivation of Representatives of Various Enzyme Classes by Glucoprotamin Measure principle: The enzyme alcohol dehydrogenase (ADH) catalyzes the reversible conversion of ethanol to acetaldehyde and simultaneously the reduction of nicotinamide adenine dinucleotide ($NAD^+$) to NADH. While the conversion of alcohol to aldehyde is not directly detectable, the formation of NADH can be optically monitored at the photometer. The increase of the absorption at 340 nm is a direct measure of the conversion of the alcohol and thus for the activity of the ADH. For testing the inactivation of the ADH by glucoprotamin 2.6% of glucoprotamin was added to commercially available in NAD-ADH reagent (NAD-ADH reagent multiple test vial; Sigma Aldrich; Germany) and incubated for 10 minutes at 37° C. Then 1% ethanol was added to the mixture as substrate and the ADH activity was determined immediately at 340 nm in an Infinite M200 microplate reader (Tecan, Switzerland). The resulting ADH kinetics was plotted in relation to the control without glucoprotamin (FIG. 1). The results shown in the ADH kinetics of the colorimetric analysis show that glucoprotamin completely inactivates the ADH.

2.2 Hydrolases (Enzyme Class 3; EC3)

Inactivation of the Alkaline Phosphatase (EC3.1.3.1)

Measurement principle: The alkaline phosphatase (ALP) catalyzes the hydrolysis of phosphate ester under alkaline conditions to organic radicals and inorganic phosphates. The detection of the ALP activity is made via the cleavage of p-nitrophenylphosphate (pNPP). The formation of the yellow nitrophenolate can directly be monitored via the measurement of the absorption at 405 nm.

Figure 2:
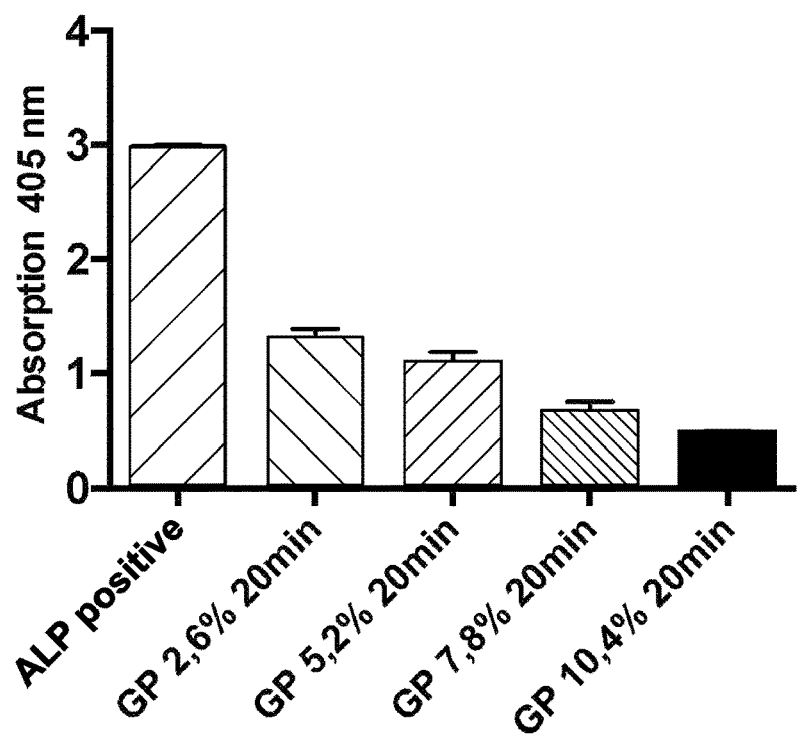
FIG. 2: Concentration-depending modulation of the alkalic phosphatase (ALP) by glucoprotamin. In comparison with the positive control without glucoprotamin (ALP positive) an incubation with glucoprotamin (GP) for 20 minutes results in an inactivation of ALP in dependence of its concentration (n=3; error bars=SEM).

For testing the inactivation of the ALP by glucoprotamin a commercially available test system (Alkaline Phosphatase Assay Kit; Abcam, USA) was employed. For this purpose, ALP contained in the kit system was incubated for 20 minutes at 37° C. with 2.6%, 5.2%, 7.8%, and 10.4% glucoprotamin. At the same time the positive control with the same enzyme concentration without glucoprotamin was used and incubated like the other samples and measured. After the addition of 1 mM pNPP the samples were incubated for further 30 minutes and then the absorption at 405 nm was determined in an Infinite M200 microplate reader (FIG. 2). The values of this end time measurement show an inactivation of the ALP by glucoprotamin, which is concentration-dependent.

Inactivation of Endoproteases

Measurement principle: The activity of endoproteases is also measured by means of a Fluorescence Resonance Energy Transfer (FRET) peptide library which contains more than 2.5 million of peptides (Kapprell et al. (2011), Assay and Drug Development Technologies). The principle of this protease detection is based on the MCA fluorophore as a donor and the 2,4-dinitrophenyl residue as a quencher, which are coupled to the peptides. As soon as the protease cleaves the peptides, the donor and the quencher are separated from each other and a strong fluorescent signal occurs. The protease activity is therefore directly proportional to the increase of the relative fluorescent intensity.

Figure 3:
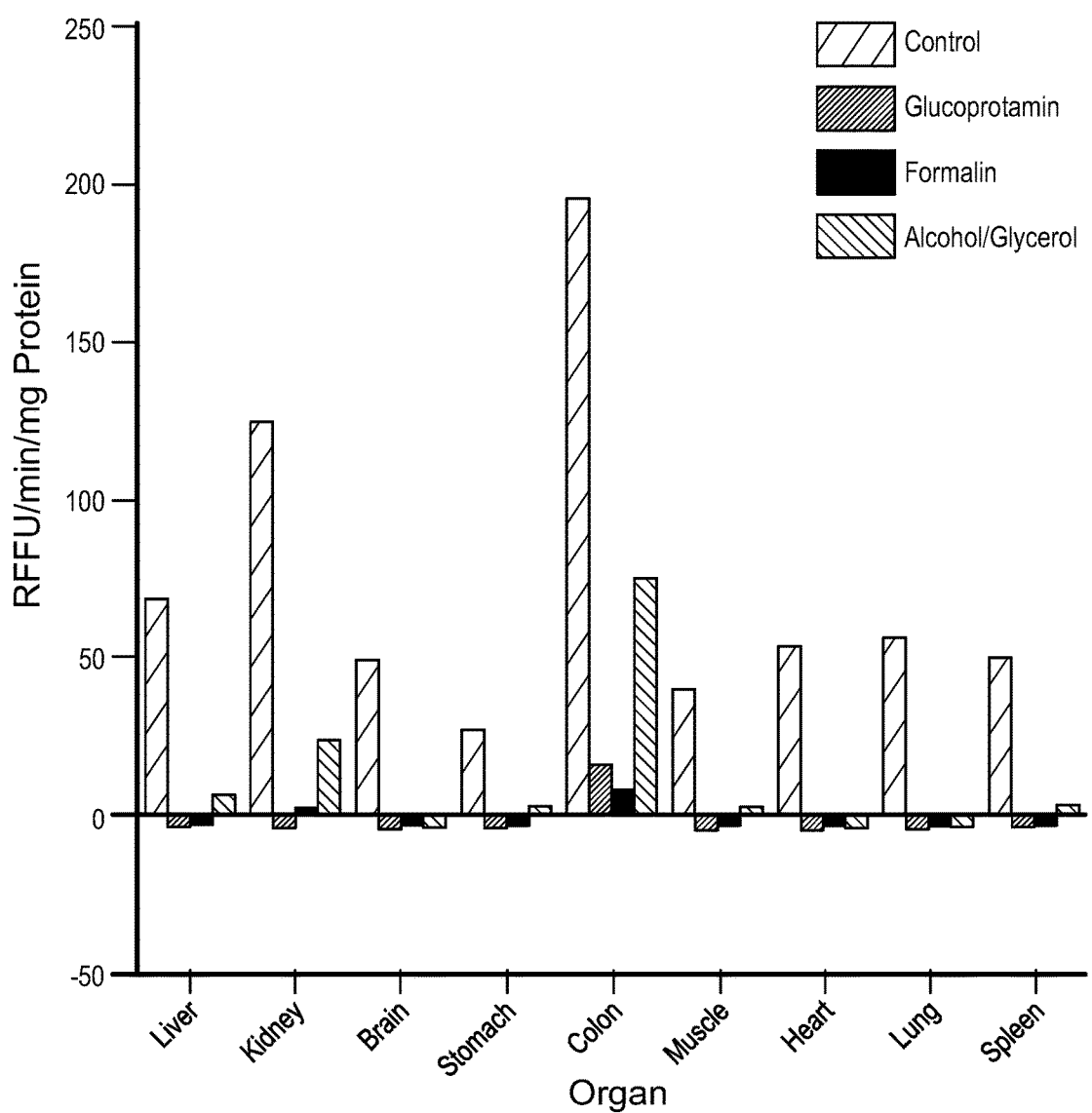
FIG. 3: Inactivation of the endoproteases by glucoprotamin in comparison with formalin and alcohol/glycerol. The treatment of various rat organs (Wistar rat; postnatal, 3 days) with glucoprotamin results in an inactivation of the endoproteases; no normalized, relative fluorescence activity (RFU/min/mg protein) could be measured like in the treatment with formalin. In the treatment with alcohol/glycerol still an activity of the endo-proteases in the kidneys and the colon could be detected (n=3).

For the determination of the inactivation of the endoproteases by glucoprotamin nine (three times each) different organs of the rat (Wistar rats, postnatal, day 3) were either incubated with 2.6% glucoprotamin, 4% formalin or an alcohol/glycerol solution (70% alcohol/30% glycerol). Then these organs were homogenized in Tris buffer (pH 7.4). Unfixed, freshly prepared organs of the rat (n=3) were used as positive control. After the determination of the protein concentration (Qubit Protein Assay, Life Technologies, Germany), the mixtures were centrifuged and 10 µl of the supernatant was added to 80 µl Tris buffer and 10 µl of the FRET-based peptide library. The relative fluorescence intensity (RFU) was immediately determined by the aid of an Infinite M200 microplate reader. The relative fluorescence intensity per time unit (gradient) normalized to the protein concentration shows an inactivation of the endoproteases by glucoprotamin which is similar to the inactivation of the endoproteases by formalin. The alcohol/glycerol fixation in the kidney and in the colon did not result in a complete inactivation of the endoproteases but only to a reduction of the activity of the proteases (FIG. 3). In the positive control in all organs an activity of endoproteases could be identified.

Inactivation of the RNases

Measurement principle: The activity of RNases can be determined by the aid of a cleavable fluorescence labeled RNase substrate according to the FRET principle (RNase-Alert lab test kit; Applied Biosystems, Germany). The substrate is a modified RNA oligonucleotide which emits green fluorescence when it is cleaved by RNases. The RNase activity is thus directly proportional to the increase of the fluorescence intensity.

Figure 4:
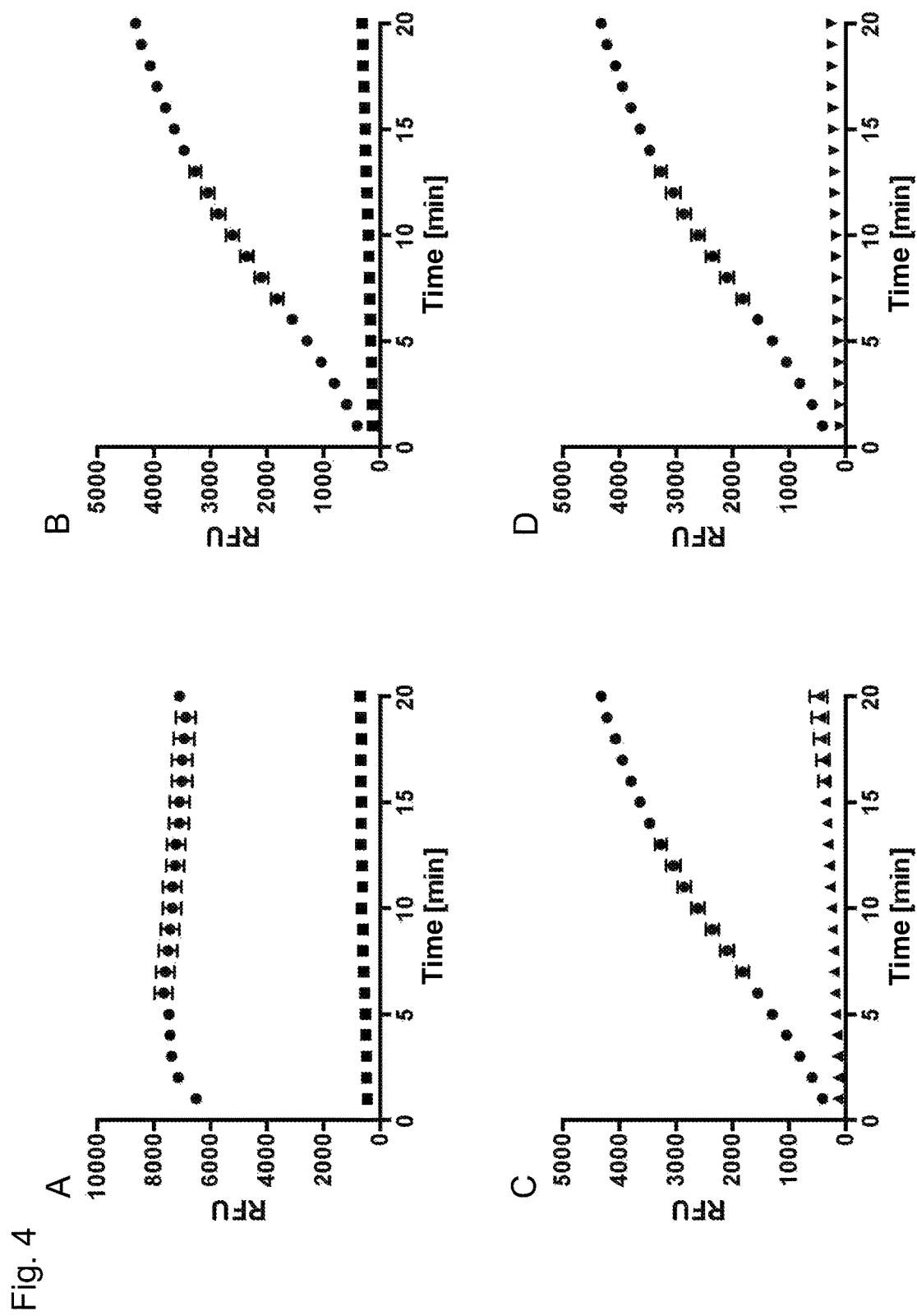
FIG. 4: Realtime detection of the inactivation of the RNases by glucoprotamin. (A) The treatment with glucoprotamin results in an inactivation of the RNase A (squares; n=3, error bars=SEM) in comparison to untreated RNase A (circles, n=3, error bars=SEM). (B) Glucoprotamin inactivates RNAses (squares, n=3, error bars=SEM) of a contaminated work area (positive control; circles, n=3, error bars=SEM). This inactivation can be compared with the decontamination effect of commercially available solutions: (C) RNAseZap (triangles, n=3, error bars=SEM) and (D) RNase-ExitusPlus (triangles, n=3, error bars=SEM). (B)-(D) Positive control (circles) work area treated with nuclease-free water.

For the determination of the inactivation of RNases by glucoprotamin two different approaches were chosen. At first 5 µl RNase A (approximately 2 pg) from a commercial test system (RNaseAlert Lab Test Kit) were added to 2.6% glucoprotamin according to the information of the manufacturer and incubated for 10 minutes at 37° C. To the positive control instead of glucoprotamin nuclease free water was added but for the rest treated in the same way. After the addition of fluorescence labeled substrate, the RNase activity was determined by the aid of an Infinite M200 microplate reader in realtime. Over the measurement period of 20 minutes, no increase of the relative fluorescence intensity (RFU) could be detected in the mixture which was treated with glucoprotamin, which then shows the inactivation of the RNase A by glucoprotamin (FIG. 4A). In the positive control a consistent RNase activity saturated with substrate could be identified.

In another approach a laboratory workplace was contaminated with human perspiration and saliva. Then the work area was separated in four areas of the same size and they were each differently treated: nuclease free water (positive control), 2.6% glucoprotamin (FIG. 4B), RNaseZap (commercial RNase decontamination solution of Blyde Biosystems; FIG. 4C) and RNase exitusPlus (commercial RNase decontamination solution of AppliChem, Germany; FIG. 4D). After incubation for 10 minutes the treated areas were rinsed two times with 500 ml nuclease free water. After drying of the areas 500 µl each of nuclease free water were evenly distributed on the working areas, incubated for one minute and removed by the aid of a pipette. The fluorescence labeled substrate was added to 45 µl of these four different mixtures and the change of the fluorescence intensity and therefore the RNase activity was determined by the aid of an Infinite M200 microplate reader (Tecan, Switzerland) in realtime (FIG. 4B-D). The treatment of the working places with glucoprotamin results in an inactivation of the RNases contained in perspiration and saliva and therefore to a decontamination of the working area. This complete decontamination can be compared to so far commercially available decontamination solutions. On the working place which was only treated with nuclease free water (positive control), however, an increase of the fluorescence intensity depending on the time and therefore a high RNase activity could be identified.

Inactivation of the Lipases

Measurement principle: The lipase hydrolyses arachidonoyl-1-thioglycerol to arachidonic acid and thioglycerol. Thioglycerol reacts with the thiofluometric detector to a strongly fluorescent product which can be analyzed at an excitation wave-length of 380 to 390 nm and an emission wavelength of 510 to 520 nm.

Figure 5:
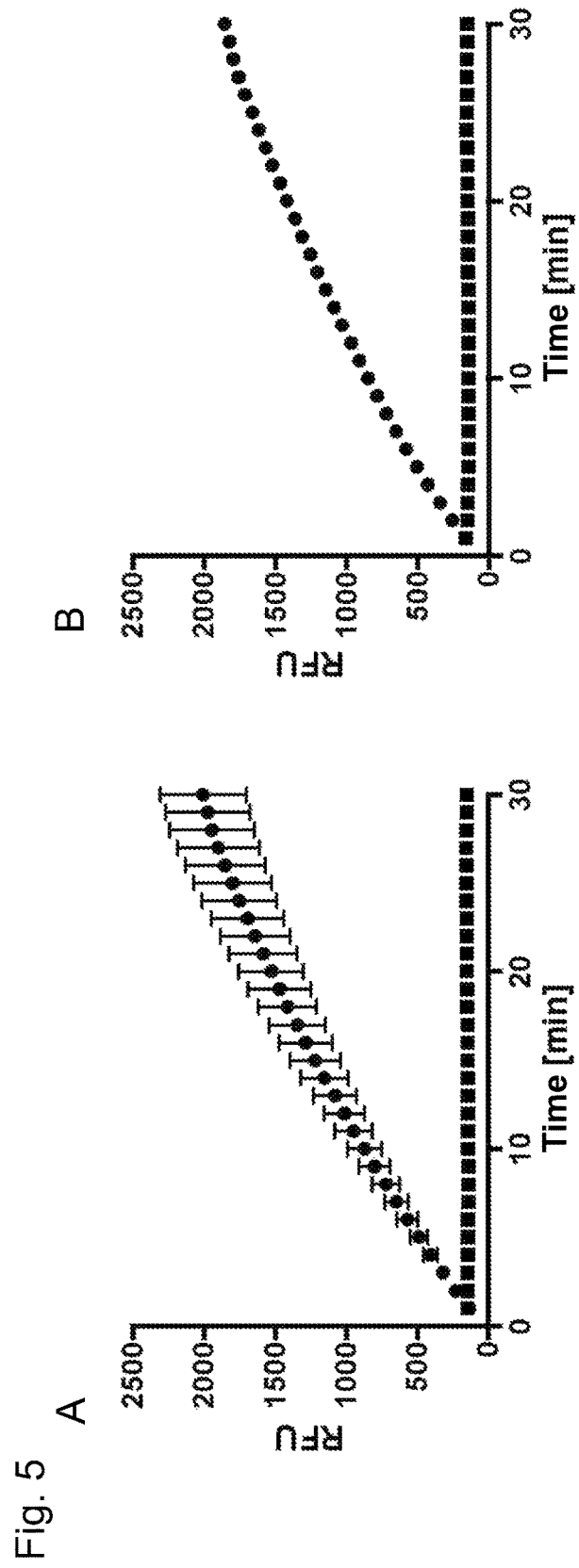
FIG. 5: Realtime detection of the inactivation of the lipases by glucoprotamin. (A) Glucoprotamin inactivates the bovine lipoprotein lipase (squares, n=3, error bars=SEM) whereas in the positive control the lipase activity relatively increases over the time (circles, n=3, error bars=SEM). (B) Glucoprotamin inactivates human lipases from subcutaneous fatty tis-sue (squares, n=3, error bars=SEM). The activity of the lipases obtained from the human fatty tissue relatively increases over the time (circles, n=3, error bars=SEM).

For the testing of the inactivation of the lipases by glucoprotamin, a commercial test system was used according to the information of the manufacturer (Lipase Activity Assay, Cayman Chemical Company, USA). Two different test processes were performed. At first 10 µl bovine milk lipoprotein lipase were supplemented with 2.6% of glucoprotamin and assay buffer and thiol detector were added according to the information of the manufacturer. In the positive control, glucoprotamin was omitted. Both solution mixtures were incubated for 15 minutes at 37° C. Then the lipase substrate was added and the lipase activity was determined by the detection of the change of fluorescence intensity (RFU) in realtime (FIG. 5A). The bovine milk lipoprotein lipases were inactivated by glucoprotamin. In a second test process, 200 mg of human, gluteal, subcutaneous fatty tissue was removed post mortem and homogenized with ice cold PBS by the aid of a Precellys ceramic kit 1.4/2.1 mm (PeqLab, Germany) in a minilysis workplace homogenizer (PeqLab) for 4×10 seconds at 5,000 rpm. The homogenate was then centrifuged for 10 minutes at 10,000×g and 10 µl of the mid phase were removed. This sample was either supplemented with 2.6% of glucoprotamin or directly (positive control) added to the assay buffer at the thiol detector. Both solution mixtures were incubated for 15 minutes at 37° C. and, as described above, the fluorescence intensity was measured in realtime (FIG. 5B). Glucoprotamin inactivates human lipases from subcutaneous fatty tissue.

Figure 6:
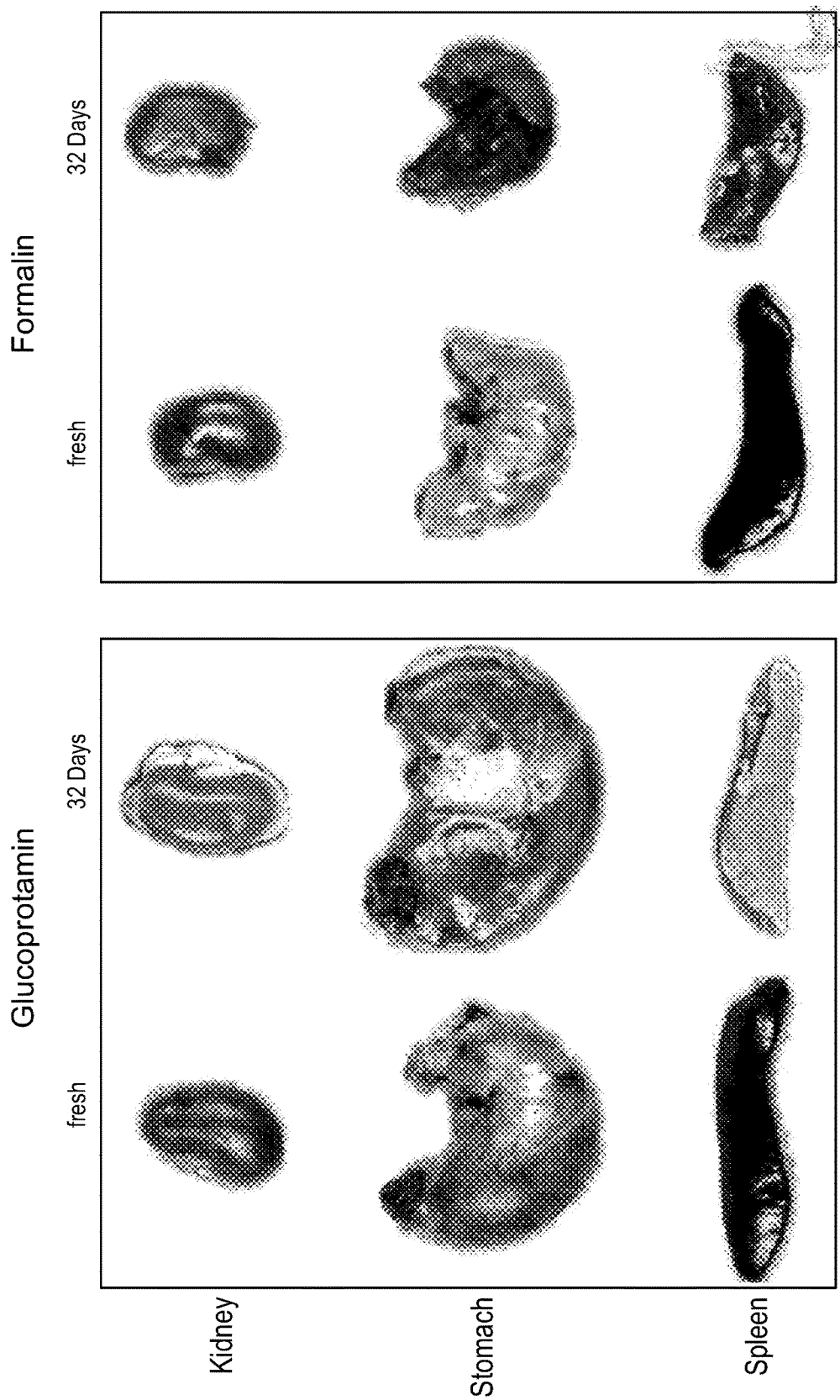
FIG. 6: Preservation of organs from the rat (Wistar, postnatal, 31 days) with glucoprotamin in comparison to the preservation with formalin.

For the detection of the preservation activity of glucoprotamin, organs were removed from adult Wistar rats (postnatal, 31 days) and photodocumented. Then the organs were either incubated in 2.6% of glucoprotamin or in 4% of formalin for 7 days. Then the organs were stored for additional 25 days without preservation solutions, uncovered at room temperature and then again photodocumented and assessed (FIG. 6). Glucoprotamin-preserved organs show a preservation which is comparable to formalin fixed organs but they maintained their tissue elasticity.

After the availability of the examination results on the single enzyme level and the results of the organ fixation in the animal model (immersion fixation after organ removal) in compliance with the practice of the anatomic body donation (Ethics Committee Vote 237/2007B01 and the Burial Law of Baden-Württemberg of 21 Jul. 1970) by analogy with the formalin fixation, the body of a body donor was infused with 17 l of a 2.5% glucoprotamin/20% ethanol solution intraarterial via the A. femoralis with a pump performance of 1 bar.

The full body preparation was wrapped into a wet cloth with a above-mentioned solution and sealed in a foil. A control of the consistency of the tissue and of the state of the tissue was made after 2 weeks, 1 month, after 3 months and after 7 months.

Inspection after 2 Weeks and 1 Month

No signs of lysis could be found, the tissue structure remained unchanged, the haptics is close to reality as opposed to the formalin fixation.

Invasive Examination after 3 Months

The diagnostic laparoscopy and then an open surgical examination via a mediane laparotomy were performed. Result: The gastrointestinal tract was intact without signs of an occurred lysis. A performed microbiological smear test showed an asepsis of the intraperitoneal space in the area of the colon and the recessus of the abdominal cavity.

In the context of an orthopedic surgery course an arthroscopy of the shoulder joint was carried out. The joint space was preserved close to reality, structures of ligaments and cartilages were close to reality with respect to haptics.

Invasive Examinations after 7 Months

Figure 7:
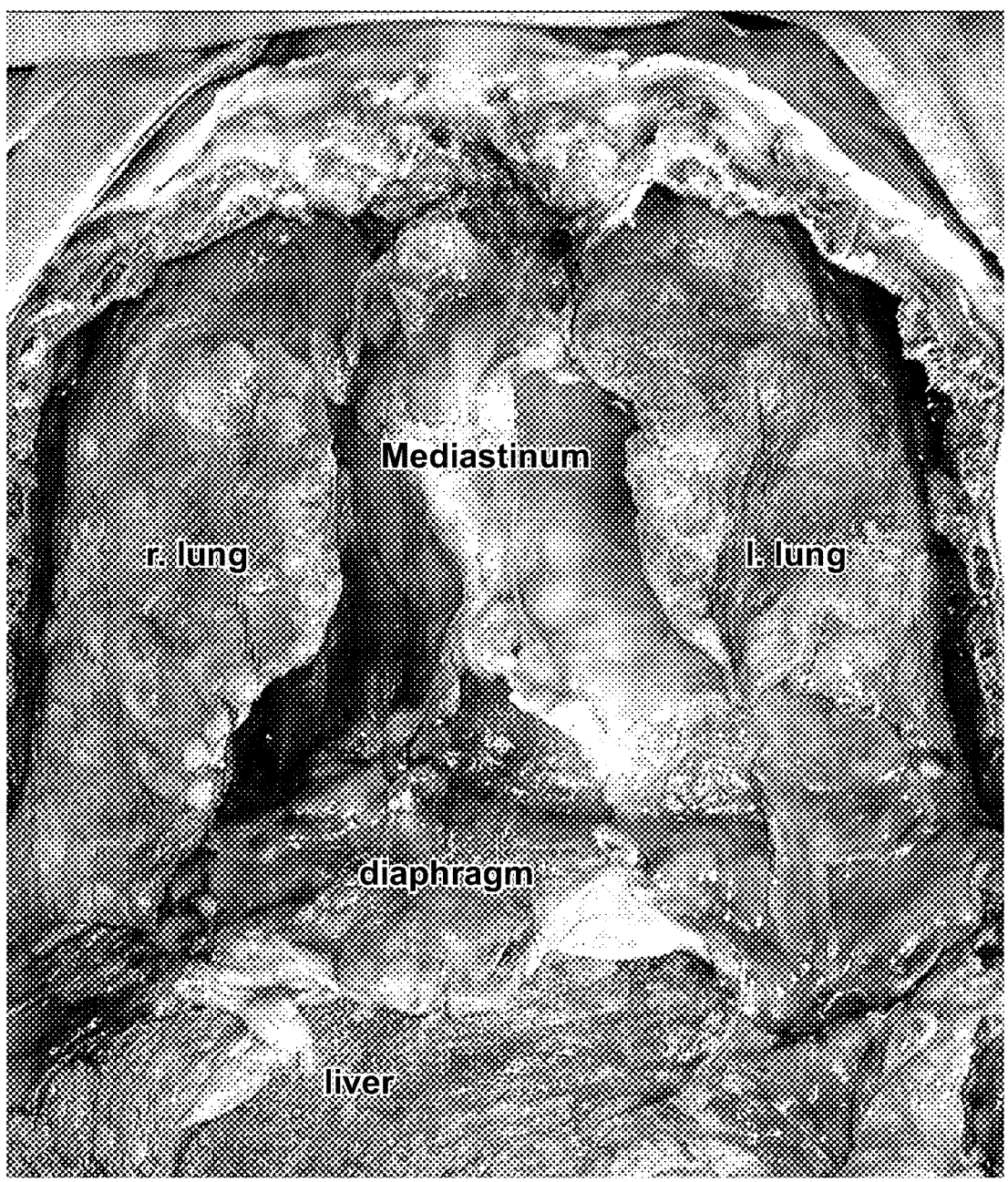
FIG. 7: Opened thorax situs of a body donor after a transarterial infusion with glucoprotamin, 7 months post mortem.
Figure 8:
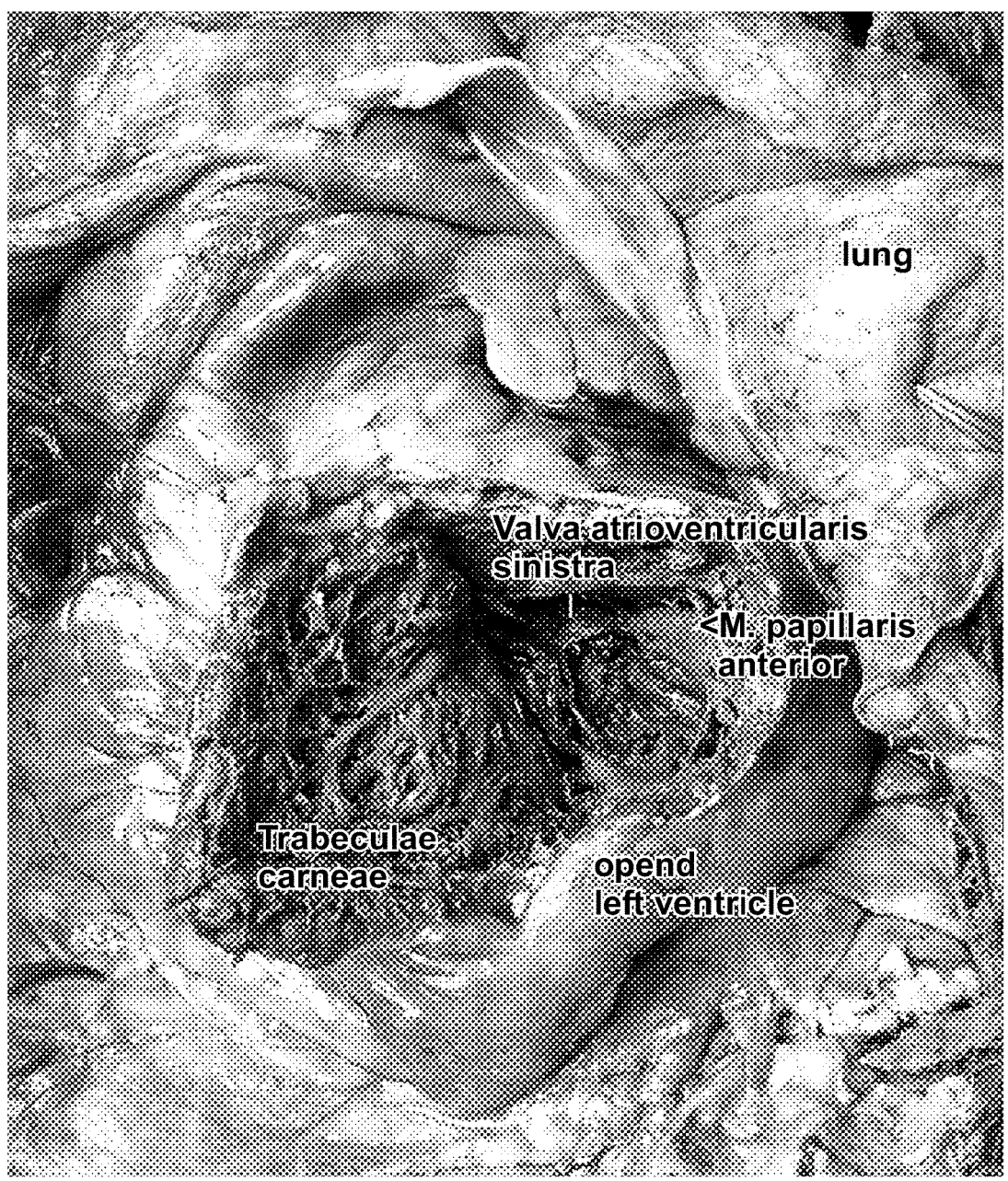
FIG. 8: Opened left heart ventricle of a body donor after transarterial infusion with glucoprotamin, 7 months post mortem.

After 7 months, an anatomical cover situs preparation was carried out (FIGS. 7 and 8) to open and inspect the entire abdominal area. All of the organs were preserved. Also the organs with a per se high content of digestive enzymes, such as the pancreas, maintained their morphological integrity. The left heart was opened and the endocardial space was inspected (FIG. 8). Even fine structures, e.g. atrioventricular valves, chordae tendineae, were preserved close to reality.

Also after 7 months, a good preservation of structure could be found without signs of an occurred lysis.

5. Conclusion

The inventors provide an active substance in form of a 5-oxo-pyrrolidine-2-carboxylic acid derivative, such as the glucoprotamin, which is versatilely applicable and by means of which the activity of non-structure proteins can be modulated, preferably inhibited. The substance is of significantly less health concerns than the currently used aldehydes, detergents and surfactants.

What is claimed is:

1. Method for the modulation of non-structural proteins, comprising the step of contacting said non-structural proteins with a composition comprising a 5-oxo-pyrrolidine-2-carboxylic acid derivative with the formula I

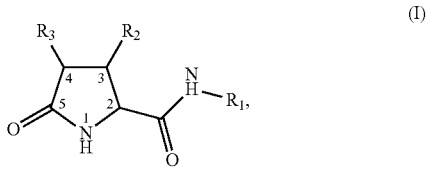

wherein
$R_1$ is selected from the group consisting of:
linear alkyl residue with $C_1$-$C_6$,

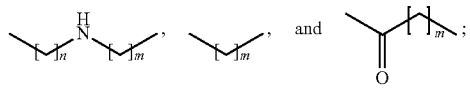

$R_2$ and $R_3$ are each independent from each other selected from the group consisting of:

with each:
n=0-20,
m=1-25, and
X=O or S.

2. Method of claim 1, wherein said modulation is an inhibition or an inactivation.

3. Method of claim 1, wherein said non-structure protein is an enzyme.

4. Method of claim 3, wherein said enzyme is selected from the group consisting of: oxidoreductases, hydrolases, transferases, lyases, isomerases, and ligases.

5. Method of claim 4, wherein said hydrolases are selected from the group consisting of: alkaline phosphatase, endoproteases, RNases, DNases, lipases.

6. Method of claim 1, wherein said 5-oxo-pyrrolidine-2-carboxylic acid derivative has the formula II wherein n=3 and m=11-15:

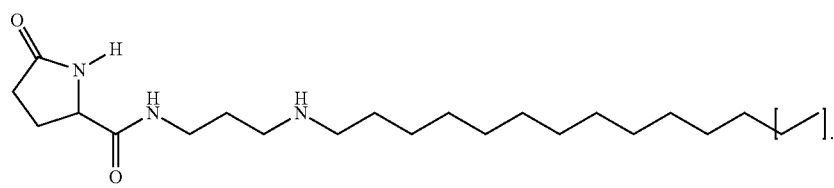

\* \* \* \* \*